United States Patent
Yasuda et al.

(10) Patent No.: US 7,678,777 B2
(45) Date of Patent: Mar. 16, 2010

(54) **COMPOSITION FOR PROMOTING THE PROLIFERATION OF *LACTOBACILLUS CASEI* SUBSP. *CASEI***

(75) Inventors: Kenji Yasuda, Ogaki (JP); Tomohiko Ogawa, Toyonaka (JP); Masakatsu Hasegawa, Nagoya (JP)

(73) Assignee: Meito Sangyo Co., Ltd., Nagoya-shi, Aichi (JP)

( * ) Notice: Subject to any disclaimer, the term of this patent is extended or adjusted under 35 U.S.C. 154(b) by 0 days.

(21) Appl. No.: 12/190,121

(22) Filed: Aug. 12, 2008

(65) Prior Publication Data

US 2008/0305090 A1 Dec. 11, 2008

Related U.S. Application Data

(62) Division of application No. 10/521,947, filed as application No. PCT/JP03/09272 on Jul. 22, 2003, now abandoned.

(30) Foreign Application Priority Data

Jul. 22, 2002 (JP) ............... 2002-212336

(51) Int. Cl.
*A61K 31/721* (2006.01)
*A61K 35/74* (2006.01)
*C08B 37/02* (2006.01)

(52) U.S. Cl. ............... 514/59; 514/54; 536/112; 536/123.1; 536/123.12; 424/93.45

(58) Field of Classification Search ............. 514/59, 514/54; 536/112, 123.1, 123.12; 424/93.45
See application file for complete search history.

(56) References Cited

U.S. PATENT DOCUMENTS 6,007,808 A * 12/1999 De Haen et al. ............ 424/93.4

FOREIGN PATENT DOCUMENTS

| EP | 0 382 355 | | 8/1990 |
|---|---|---|---|
| EP | 382355 | A2 * | 8/1990 |
| EP | 0 726 272 | | 8/1996 |
| JP | 02-289520 | | 11/1990 |
| JP | 06-217761 | | 8/1994 |
| JP | 08-196268 | | 8/1996 |
| JP | 2000-270784 | | 10/2000 |
| JP | 2001-269125 | | 10/2001 |

OTHER PUBLICATIONS

Ogawa, et al. "Natural Kill Cell Activities of Synbiotic *Lactobacillus casei* ssp. *casei* in Conjunction with Dextran," *Clinical and Experimental Immunology*, vol. 143, No. 1, pp. 103-109, Jan. 2006.
Ogawa, et al. "A New Synbiotic, *Lactobacillus casei* subsp. *casei* Together with Dextran, Reduces Murine and Human Allergic Reaction," *FEMS Immunology and Medical Microbiology*, vol. 46, No. 3, pp. 400-409, Apr. 2006.
Ogawa, et al. "Dextran Tokui Shikasei Nyusankin o Mochiita Synbiotics ni yoru Keiko-Teki Men, Eki Zokyo Sayo," *Japanese Journal of Bacteriology*, vol. 58, No. 1, Feb. 28, 2003 with partial English translation.
Supplementary European Search Report dated Apr. 25, 2006.
Office Action mailed Jun. 6, 2006 issued to a corresponding Japanese application (2004-522778) with English translation.

* cited by examiner

*Primary Examiner*—Shaojia Anna Jiang
*Assistant Examiner*—Michael C Henry
(74) *Attorney, Agent, or Firm*—Knobbe, Martens, Olson & Bear, LLP (57) ABSTRACT

A composition for promoting bacterial proliferation and selectively proliferating *Lactobacillus casei* subsp. *casei* is disclosed, which includes a dextran. A variety of biological activities originating from *L. casei* subsp. *casei* can be sustained in a living body by selectively growing-proliferating and colonizing *L. casei* subsp. *casei* in the intestine of a human being, animal, or the like or by selectively growing-proliferating *L. casei* subsp. *casei* in the intestine, without supplying *L. casei* subsp. *casei* at all times.

4 Claims, 5 Drawing Sheets

COMPOSITION FOR PROMOTING THE PROLIFERATION OF *LACTOBACILLUS CASEI* SUBSP. *CASEI*

RELATED APPLICATIONS

This application is a divisional of U.S. application Ser. No. 10/521,947, filed Feb. 24, 2005, which is the U.S. National Phase under 35 U.S.C. §371 of International Application PCT/JP2003/009272, filed Jul. 22, 2003, which was published in a language other than English, which claims priority of Japanese Patent Application No. 2002-212336, filed Jul. 22, 2002.

TECHNICAL FIELD

The present invention relates to: a dextran-comprising composition for promoting bacterial proliferation for selectively proliferating *Lactobacillus casei* subsp. *casei* (hereinafter, abbreviated as "*L. casei* subsp. *casei*") which is one species of lactic acid bacteria having a variety of biological activities; and the composition for promoting bacterial proliferation, which further comprises *L. casei* subsp. *casei*. More specifically, the present invention relates to: a pharmaceutical composition for enhancing biological activities, which comprises the composition for promoting bacterial proliferation; and a health food and feed for enhancing biological activities, which comprise the composition for promoting bacterial proliferation.

BACKGROUND ART

Recently, ingestion of "microorganism formulations" which are referred to as probiotics and consist of useful microorganisms such as living lactic acid bacteria for the purpose of effect of controlling intestinal function, prevention of infectious diseases, immunostimulation, or the like has been attracting attraction. However, there is a doubt whether the useful microorganisms can grow and colonize in the intestine of a human being, animal, or the like. If the useful microorganisms cannot grow and colonize in the intestine, expected biological activities of the useful microorganisms cannot be obtained permanently. In order to solve such a problem, the fact is that supplying the microorganism formulation at all times is proposed and performed. On the other hand, oligosaccharides or the like which can be utilized by useful microorganisms in probiotics are referred to as prebiotics, and ones prepared by combining prebiotics and probiotics are referred to as symbiotics. Those are also administered to a human being, animal, or the like for the aforementioned purpose. However, when the prebiotics are utilized by great many enteric bacteria other than intended bacteria, those bacteria scramble for the prebiotics in the intestine, so it is difficult to grow and colonize intended useful microorganisms selectively.

DISCLOSURE OF THE INVENTION

An object of the present invention is, after ingestion of useful microorganisms referred to as probiotics to a human being, animal, or the like, to sustain a variety of biological activities originated from the useful microorganisms in a living body by selectively growing-proliferating and colonizing the microorganisms in the intestine or by selectively growing-proliferating useful indigenous microorganisms in the intestine without supplying those useful microorganisms at all times.

The inventors of the present invention have found out through an in vitro test that, among many useful microorganisms, *L. casei* subsp. *casei* is a species of bacteria capable of growing-proliferating by utilizing a dextran. *L. casei* subsp. *casei* is classified and named in Approved Lists (1980). The bacterium is Gram positive, indigenous to the intestine of a human being, animal, or the like, and a facultative anaerobic bacillus. The bacterium forms the intestinal bacterial flora together with other bacteria.

Thus, at first, it was confirmed whether or not the bacterium itself has biological activities, for example, an immunostimulating effect in the case of subcutaneous immunization. As a result, the bacterium has been found to enhance and maintain humoral immunity and cellular immunity. Next, *L. casei* subsp. *casei* has been administered to a mouse only in the initial administration, and a dextran was then orally ingested permanently, in order to confirm whether *L. casei* subsp. *casei* can selectively grow-proliferate and colonize in the intestine of a human being, animal, or the like, and the biological activities of the bacterium can be sustained or not by oral ingestion of a dextran. As a result, the inventors of the present invention have found through an in vivo test that the bacterium grows-proliferates and colonizes in the intestine by utilizing the dextran, and the biological activities of the bacterium such as humoral immunity and cellular immunity are enhanced and maintained.

On the other hand, a dextran itself is also known to have a variety of biological activities, and it has been confirmed that, in the case of administration of a dextran together with *L. casei* subsp. *casei*, a higher effect is maintained than that in the case of administration of only a dextran, and a synergistic effect is large.

The present invention has been accomplished as described above. The gist of the present invention is as follows.

(1) A composition for promoting bacterial proliferation for selectively proliferating *Lactobacillus casei* subsp. *casei*, comprising a dextran.

(2) The composition for promoting bacterial proliferation according to (1), further comprising *Lactobacillus casei* subsp. *casei*.

(3) The composition for promoting bacterial proliferation according to (1), wherein the dextran has a molecular weight of 2,000 to 40,000,000.

(4) A pharmaceutical composition comprising the composition for promoting bacterial proliferation according to any one of (1) to (3).

(5) A health food comprising the composition for promoting bacterial proliferation according to any one of (1) to (3).

(6) A feed comprising the composition for promoting bacterial proliferation according to any one of (1) to (3).

BEST MODE FOR CARRYING OUT THE INVENTION

The composition of the present invention is a dextran-comprising composition for promoting bacterial proliferation for selectively proliferating *L. casei* subsp. *casei* and the composition for promoting bacterial proliferation, which further comprises *L. casei* subsp. *casei*. Dextrans to be used in the composition of the present invention can be synthesized, prepared, or the like according to a general method that is well known to a person skilled in the art. Moreover, culture of *L. casei* subsp. *casei*, methods of preparing and drying of bacterial cells, gene recombination, and the like can be performed according to a general method that is well known to a person skilled in the art.

(Description of Dextran to be Used in the Present Invention)

A dextran is a polysaccharide which consists of glucose, which are mainly bonded with an α-1,6 bond. The dextrans to be used in the present invention may be commercially available dextrans or dextrans obtained by culturing bacteria selected from the group consisting of genus *Leuconostoc* and genus *Streptococcus*, for example, *Leuconostoc mesenteroides*, under a general condition, for example, in a sucrose-containing enriched medium.

(Molecular Weight of Dextran to be Used in the Present Invention)

Each of the molecular weights of dextrans to be used in the present invention is 2,000 to 40,000,000, preferably 4,000 to 5,000,000, more preferably 4,000 to 2,000,000. Note that a dextran having a molecular weight of less than 2,000 is not preferable because bacteria other than *L. casei* subsp. *casei* may proliferate. Examples of the dextrans to be used in the present invention include a dextran obtained by culturing the aforementioned bacteria without any treatment, and a dextran having an appropriate molecular weight obtained by further partial hydrolysis treatment of such a dextran.

(*L. casei* subsp. *casei* to be used in the Present Invention)

In the present invention, *L. casei* subsp. *casei* can be used in the form of viable cells, dried cells capable of growing-proliferating, or the like. As *L. casei* subsp. *casei* to be used in the present invention, there can be used a recombinant of *L. casei* subsp. *casei* which has at least a utilizing ability for a dextran in the composition for promoting bacterial proliferation of the present invention, in addition to a wild type. There can also be used a recombinant obtained by transducing a gene which participates in a dextran-utilizing ability originated from *L. casei* subsp. *casei* to another bacterium. Preferably, the recombinant is a novel bacterium in which a new biological activity is expressed by gene recombination of *L. casei* subsp. *casei* or another novel bacterium obtained by transducing a gene which participates in a dextran-utilizing ability originated from *L. casei* subsp. casei to another bacterium.

The composition of the present invention is a dextran-comprising composition for promoting bacterial proliferation for selectively proliferating *L. casei* subsp. *casei* and the composition for promoting bacterial proliferation which further comprises *L. casei* subsp. *casei*. The composition of the present invention can be prepared, administered, or the like according to a general method which is well known to a person skilled in the art except that the composition comprises a dextran or further comprises *L. casei* subsp. *casei*.

(Dosage Form of Composition of the Present Invention)

The composition of the present invention may be a dextran only or a mixture of a dextran and *L. casei* subsp. *casei*. Preferably, the composition of the present invention can be provided as a composition in the form of solid, semi-solid, or liquid containing a dextran in combination with a diluent, carrier, or the like which is pharmaceutically well known and pharmaceutically acceptable, or a composition in the form of solid, semi-solid, or liquid containing a dextran and *L. casei* subsp. *casei*. Note that the composition of the present invention includes: a form in which the dextran of the present invention and *L. casei* subsp. *casei* have already been combined; and a form in which the dextran of the present invention and *L. casei* subsp. *casei* have been separately processed, and are combined when the composition is used. The amount of a diluent, carrier, or the like in the composition of the present invention is appropriately varied in accordance with a purpose or usage, and is not particularly limited. In general, the amount is, for example, about 0.1 to about 99.9% by weight, preferably about 1 to about 99% by weight, more preferably about 5 to about 95% by weight based on the weight of the composition.

Note that, when a dextran and *L. casei* subsp. *casei* are simultaneously present in the form of liquid, the dextran content reduces gradually due to bacterial utilization of the dextran, so simultaneous presence of them for a long time is preferably avoided. So, it is desirable that those be separately processed and packed, and the resultant products be mixed when they are ingested, or be separately ingested.

The pharmaceutical composition of the present invention may be the composition of the present invention itself without other components. However, preferably, the composition may be one prepared in combination with a diluent, carrier, or the like, which is pharmaceutically well known and pharmaceutically acceptable, into a dosage form such as a soft capsule, hard capsule, granule, pill, powder, tablet, syrup, troche, or elixir. A method of preparing the composition into such a dosage form is well known to a person skilled in the art. When the composition is prepared into such a dosage form, a diluent, carrier, or the like which is suitable to each dosage form, pharmaceutically well known, and pharmaceutically acceptable may further be contained.

The pharmaceutical composition of the present invention can be used as a drug which aims at sustaining a variety of biological activities originated from *L. casei* subsp. *casei* in a living body by: selectively growing-proliferating and colonizing *L. casei* subsp. *casei* in the intestine of a human being, animal, or the like; or selective growth-proliferation of *L. casei* subsp. *casei* in the intestine, which is indigenous to the intestine.

When the pharmaceutical composition of the present invention is prepared, the addition amount of the composition of the present invention may be appropriately determined with reference to the description which relates to the dose and dosage cycle of the composition of the present invention described below.

The health food of the present invention is one containing the composition of the present invention and a composition such as a food or beverage. Note that the health food of the present invention includes: a form in which the composition of the present invention and a composition such as a food or beverage have already been combined; and a form in which the composition of the present invention and a composition such as a food or beverage have been separately processed, and are combined when the composition is ingested. Examples of such a food or beverage include: confectioneries such as candy, chocolate, and biscuit; breads; noodles; beverages in the form of powder, liquid, and the like; dairy products such as yogurt. In particular, in the case of yogurt, yogurt can be produced using such *L. casei* subsp. *casei*, and it is desirable that a dextran be mixed when they are ingested or be individually ingested.

The feed of the present invention contains the composition of the present invention and formula feed of livestocks, fowls, fishes, pets, or the like. Note that the feed of the present invention includes: a form in which the composition of the present invention and a feed composition have already been combined; and a form in which the composition of the present invention and a feed composition have been separately processed, and are combined when the composition is ingested.

The health food or feed of the present invention can be used for sustaining a variety of biological activities originated from *L. casei* subsp. *casei* in a living body by: selective growth-proliferation and colonization of *L. casei* subsp. *casei* in the intestine of a human being, animal, or the like; or selective growth-proliferation of *L. casei* subsp. *casei* in the intestine, which is indigenous to the intestine.

When the health food or feed of the present invention is prepared, the addition amount of the composition of the present invention may be appropriately determined with reference to the description which relates to the dose and dosage cycle of the composition of the present invention described below.

(Dose and Dosage Cycle of Composition of the Present Invention)

The dose of the composition of the present invention is, in terms of the dose of a dextran in the composition, 0.01 mg to 2 g/kg weight·day, preferably 0.1 mg to 1 g/kg weight·day, more preferably 1 mg to 100 mg/kg weight·day, and it is preferable that at least a composition comprising the dextran of the present invention be generally administered every day. Note that *L. casei* subsp. *casei* is originally a bacterium which is indigenous to the intestine of a human being, animal, or the like, and in order to induce the reliable effects of the biological activities of *L. casei* subsp. *casei*, viable cells or dried cells capable of growing-proliferating are administered at least once, preferably at an appropriate interval. In addition, in order to induce more reliable effects, those cells may be administered every day.

(Applicable Target of Composition of the Present Invention)

The composition of the present invention can be targeted for all living beings such as mammals including a human being, aves, reptiles, fishes, crustaceans, and insects.

(Biological Activity Expected to be Imparted and/or Improved by Composition of the Present Invention)

The following effects are expected: in addition to an immunostimulating effect, generally mentioned biological activities of lactic acid bacteria such as antitumor, antihypertension, antioxidation, antiulcer, anti-HIV, improvement of lipid metabolism, suppression of recurrent malignant tumor, anti-inflammation, prevention and suppression of autoimmune disease, decrease of serum cholesterol, decrease of blood glucose, suppression of producing IgE antibody, antiallergy, promotion of producing interleukin 12, promotion of absorbing mineral, enrichment of mineral, regulation of alcohol absorption and metabolism, prevention and treatment of urinary tract infection, suppression of producing harmful matter, control of intestinal function, prevention of constipation, beauty, treatment and prevention of hyperammonemia and hepatic encephalopathy, or the like, prevention of infection, suppression of feces malodor, decrease of intestinal pH of livestocks, fowls, improvement of growth, promotion of fattening, and help of egg laying.

EXAMPLES

Hereinafter, the present invention is described in more detail by way of examples, but the present invention is not limited thereto.

Example 1

Dextran Preparation Method Using Sucrose as Principal Material

*Leuconostoc mesenteroides*, which is one species of lactic acid bacteria, was inoculated in a medium containing sucrose as a principal material (sucrose-containing enriched medium), and cultured anaerobically at 25° C. for 24 hours. Subsequently, methanol was added to the culture supernatant, and the resultant precipitates were dissolved in distilled water. After the insolubles had been removed, methanol was added thereto again, and the resultant precipitates were redissolved in distilled water. The mixture was subjected to spray drying, to thereby yield a dextran. The dextran was further partially hydrolyzed, and the resultant products were subjected to methanol fractionation and spray drying, to thereby yield dextrans having a variety of molecular weights.

Example 2

Test of Dextran-Utilizing Ability of Enteric Bacteria

A variety of related enteric bacteria were inoculated in a PYF medium (Peptone yeast extract Fildes solution broth) to which a dextran having a molecular weight (number average) of 10,000 (in the following examples, a dextran having such a molecular weight was used unless otherwise defined) was added to 0.5%, and the dextran-utilizing ability was determined. As a result, two strains of *L. casei* subsp. *casei* (JCM 1134 and JCM 8129) were confirmed to have the dextran-utilizing ability. However, no dextran-utilizing ability was observed for other lactic acid bacteria such as bacteria of the genus *Lactobacillus* or *Bifidobacterium*, and other related enteric bacteria. (See Table 1)

TABLE 1

Dextran-utilizing ability of related enteric bacteria

| Bacterial name | | Bacterial strain name | Dextran-utilizing ability |
|---|---|---|---|
| *Lactobacillus* | *casei* subsp. *casei* | JCM 1134 | + |
| | *casei* subsp. *casei* | JCM 8129 | + |
| | *acidophilus* | #527 | − |
| | *acidophilus* | JCM 1132 | − |
| | *agilis* | JCM 1187 | − |
| | *amylovorus* | JCM 1126 | − |
| | *aviarius* subsp. *aviarius* | JCM 5666 | − |
| | *brevis* | JCM 1059 | − |
| | *buchneri* | JCM 1115 | − |
| | *casei* subsp. *alactosus* | JCM 1133 | − |
| | *casei* subsp. | JCM 1177 | − |

TABLE 1-continued

Dextran-utilizing ability of related enteric bacteria

| Bacterial name | | Bacterial strain name | Dextran-utilizing ability |
|---|---|---|---|
| | fusiformis | | |
| | casei subsp. plantarum | JCM 8136 | – |
| | casei subsp. pseudoplantarum | JCM 1161 | – |
| | casei subsp. rhamnosus | JCM 1136 | – |
| | crispatus | JCM 1185 | – |
| | curvatus | JCM 1096 | – |
| | delbrueckii subsp. bulgaricus | JCM 1002 | – |
| | delbrueckii subsp. lactis | JCM 1248 | – |
| | fermentum | JCM 1173 | – |
| | gallinarum | JCM 2011 | – |
| | gasseri | JCM 1131 | – |
| | johnsonii | JCM 2012 | – |
| | oris | JCM 11028 | – |
| | paracasei subsp. paracasei | JCM 1053 | – |
| | plantarum | IFO 3070 | – |
| | reuteri | JCM 1112 | – |
| | salivarius subsp. salicinius | JCM 1150 | – |
| | salivarius subsp. salivarius | JCM 1231 | – |
| Clostridium | butyricum | JCM 1391 | – |
| | perfringens | JCM 1290 | – |
| Klebsiella | pneumoniae subsp. pneumoniae | JCM 1662 | – |
| Fusobacterium | varium | JCM 3722 | – |
| Enterococcus | faecalis | JCM 5803 | – |
| | faecium | JCM 5804 | – |
| Eubacterium | limosum | JCM 6421 | – |
| Propionibacterium | acnes | JCM 6425 | – |
| Bacteroides | fragilis | ATCC 25285 | – |
| Escherichia | coli | IFO 3972 | – |
| Bacillus | subtilis subsp. subtilis | IFO 3134 | – |
| Bifidobacterium | adolescentis | JCM 1275 | – |
| | angulatum | JCM 7096 | – |
| | animalis | JCM 1190 | – |
| | asteroides | JCM 8230 | – |
| | bifidum | JCM 1209 | – |
| | boum | JCM 1211 | – |
| | breve | JCM 1192 | – |
| | catenulatum | JCM 1194 | – |
| | choerinum | JCM 1212 | – |
| | coryneforme | JCM 5819 | – |
| | cuniculi | JCM 1213 | – |
| | dentium | JCM 1195 | – |
| | gallicum | JCM 8224 | – |
| | gallinarum | JCM 6291 | – |
| | indicum | JCM 1302 | – |
| | infantis | JCM 1222 | – |
| | longum | JCM 1217 | – |
| | magnum | JCM 1218 | – |
| | merycicum | JCM 8219 | – |
| | minimum | JCM 5821 | – |
| | pseudocatenulatum | JCM 1200 | – |
| | pseudolongum subsp. globosum | JCM 5820 | – |
| | pseudolongum subsp. pseudolongum | JCM 1205 | – |
| | pullorum | JCM 1214 | – |
| | ruminantium | JCM 8222 | – |
| | saeculare | JCM 8223 | – |
| | subtile | JCM 5822 | – |
| | suis | JCM 1269 | – |
| | thermophilum | JCM 1207 | – |

Moreover, using two strains of *L. casei* subsp. *casei*, a difference of the utilizing abilities according to dextrans having different molecular weights was determined. As a result, for all tested dextrans, the dextran-utilizing abilities were confirmed. However, a dextran having a smaller molecular weight has a tendency to be more utilized. (See Table 2)

TABLE 2

Difference of utilizing ability according to dextran molecular weight

| Dextran | *L. casei* subsp. *casei* | |
|---|---|---|
| Molecular weight | JCM 1134 | JCM 8129 |
| 2,000 | +++ | +++ |
| 4,000 | +++ | +++ |
| 7,000 | ++ | ++ |
| 10,000 | ++ | ++ |
| 14,000 | ++ | ++ |
| 40,000 | ++ | ++ |
| 200,000 | + | + |
| 2,000,000 | + | + |

Example 3

Figure 1:
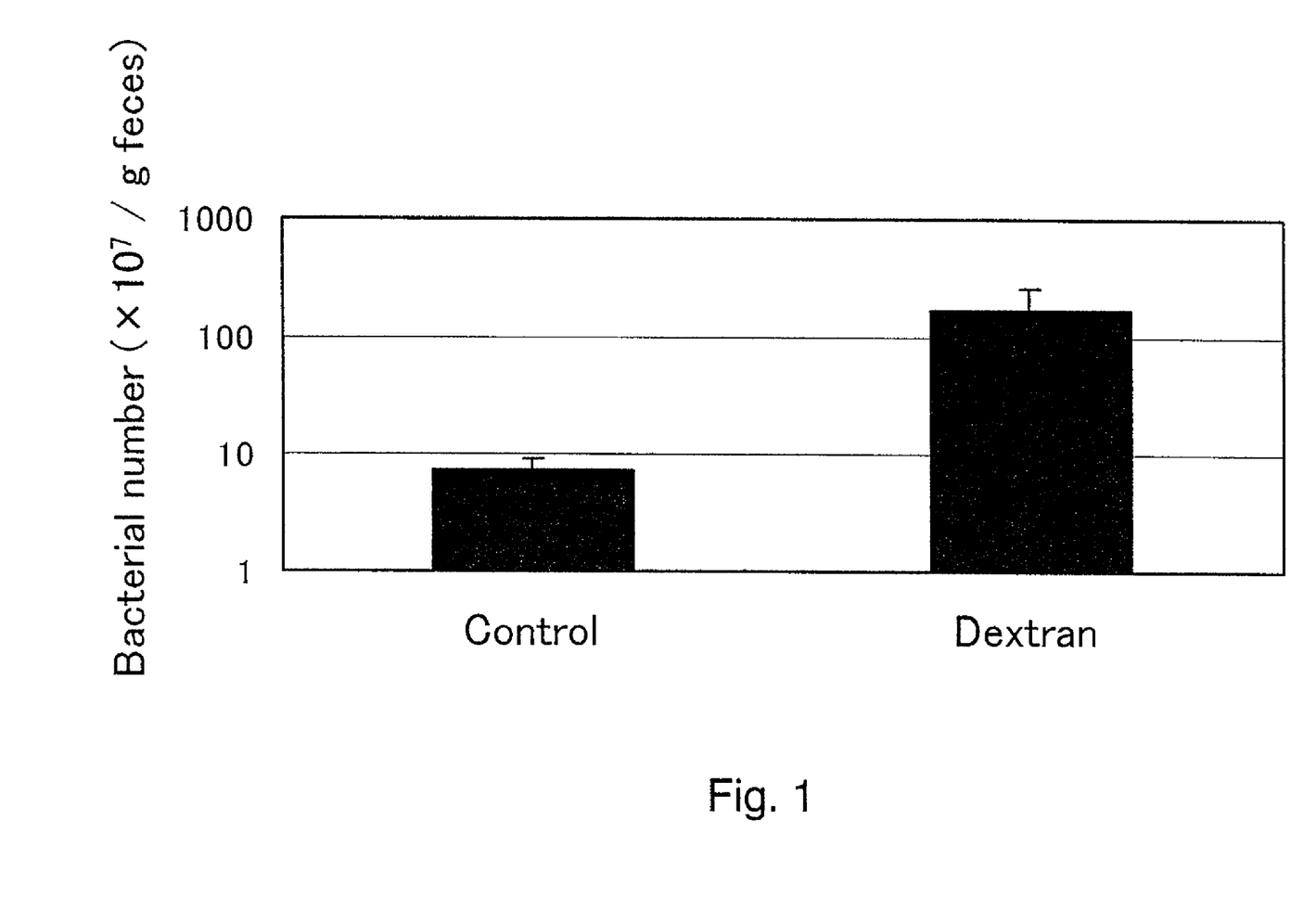
FIG. 1 is a drawing showing an effect of a dextran on the bacterial number of *L. casei* subsp. *casei* in mouse feces.

Effect of Dextran on Bacterial Number of *L. Casei* subsp. *casei* in Mouse Feces 12 eight-week-old BALB/c male mice were divided into two groups of six each. Those groups were referred to as (1) control group and (2) dextran group. Over the test period from the beginning of the test, a conventional feed was given to (1), while a dextran-added conventional feed (75 mg dextran/kg conventional feed) was given to (2). Over the period of three days from the beginning of the test, *L. casei* subsp. *casei* cells were orally inoculated to both groups ($10^6$ cells/mouse). On 28th day, each mouse was dissected, and the feces were collected from the large intestine. The feces were serially diluted with phosphate buffered saline (PBS), and the resultant mixture was smeared on a dextran-added LB medium, followed by culture at 37° C. for 48 hours. After colonies had been stained by Gram staining and observed, the bacterial number of *L. casei* subsp. *casei* in feces was counted. As a result, the bacterial number of *L. casei* subsp. *casei* in the dextran group was significantly larger than that in the control group. (See FIG. 1)

Example 4

Figure 2:
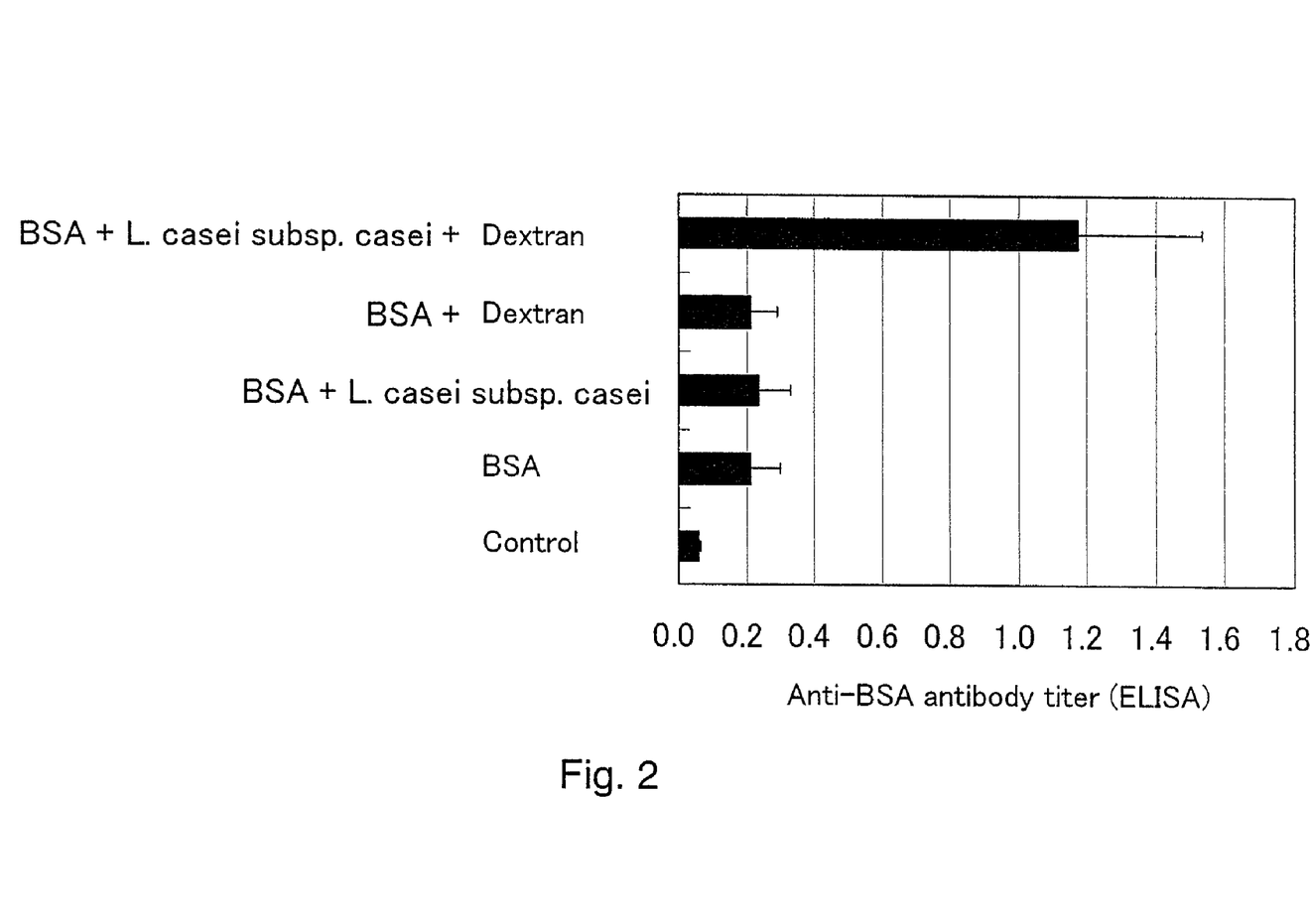
FIG. 2 is a drawing showing the results of enhancing humoral immunity by a dextran in the case of orally administering an antigen.

Enhancement of Humoral Immunity by Dextran in Oral Administration of Antigen 30 eight-week-old BALB/c male mice were divided into five groups of six each. Those groups were referred to as (1) control group, (2) BSA (bovine serum albumin) group, (3) BSA+*L. casei* subsp. *casei* group, (4) BSA+dextran group, and (5) BSA+*L. casei* subsp. *casei*+dextran group. Over the test period from the beginning of the test, a conventional feed was given to each of (1), (2), and (3), while a dextran-added conventional feed (75 mg dextran/kg conventional feed) was given to each of (4) and (5). Over the period of three days from the beginning of the test, *L. casei* subsp. *casei* cells were orally inoculated to (3) and (5) ($10^6$ cells/mouse). On third and forth days, BSA was dissolved in PBS at a concentration of 10 mg/ml, and the solution was orally administered (1 mg (100 µl)/mouse) to (2) to (5). On 33rd and 34th days, in a manner similar to that on the third and forth days, BSA was orally administered (1 mg/mouse). Five days after the administration, the blood was drawn from the suborbital vein, and the anti-BSA antibody titer was determined by ELISA. As a result, in (5) BSA+*L. casei* subsp. *casei*+dextran group, the specific antibody titer was significantly high. (See FIG. 2)

Example 5

Figure 3:
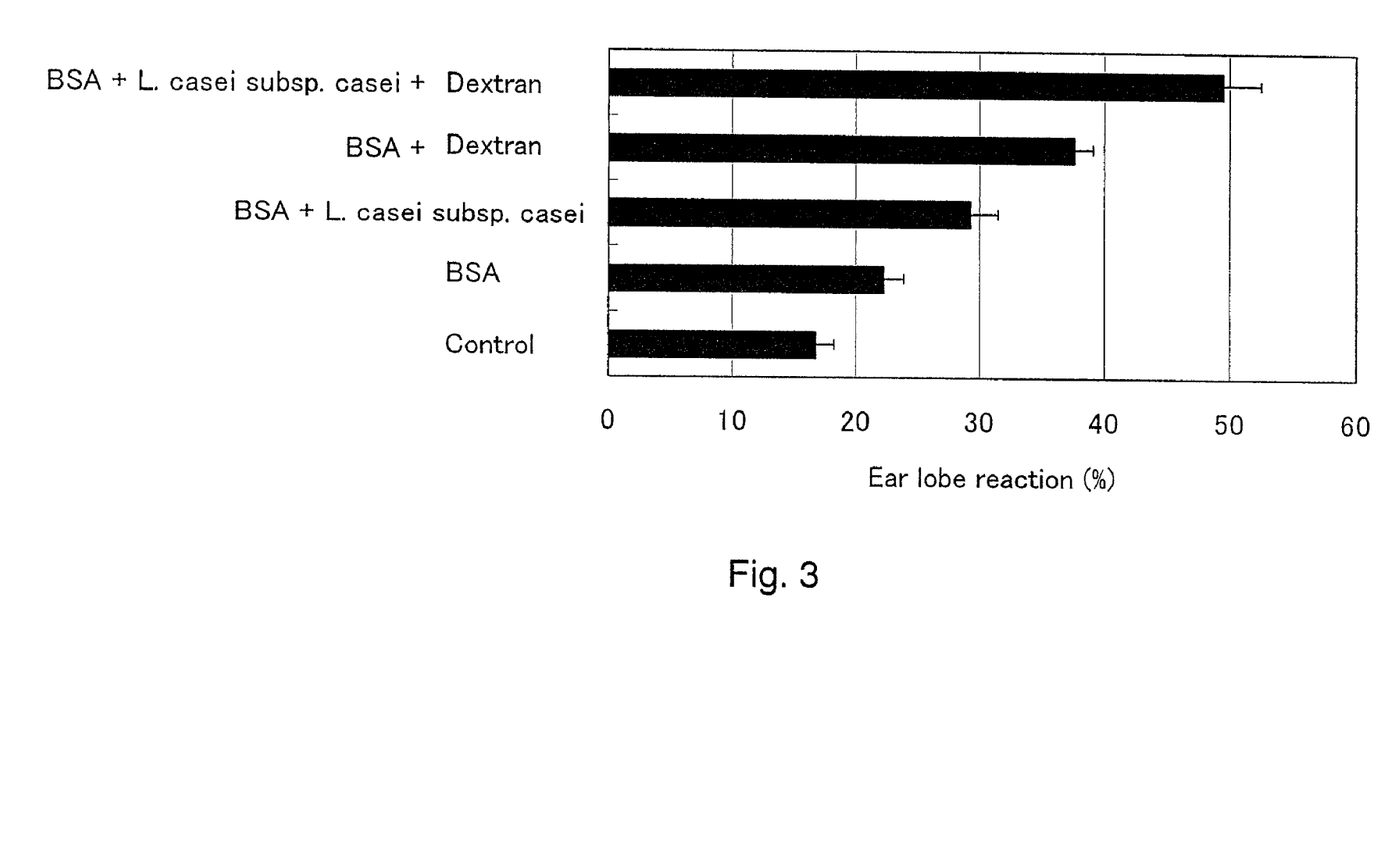
FIG. 3 is a drawing showing the results of enhancing cellular immunity by a dextran in the case of orally administering the antigen.

Enhancement of Cellular Immunity by Dextran in Oral Administration of Antigen 30 eight-week-old BALB/c male mice were divided into five groups of six each. Those groups were referred to as (1) control group, (2) BSA group, (3) BSA+*L. casei* subsp. *casei* group, (4) BSA+dextran group, and (5) BSA+*L. casei* subsp. *casei*+dextran group. Over the test period from the beginning of the test, a conventional feed was given to each of (1), (2), and (3), while a dextran-added conventional feed (75 mg dextran/kg conventional feed) was given to each of (4) and (5). Over the period of three days from the beginning of the test, *L. casei* subsp. *casei* cells were orally inoculated to (3) and (5) ($10^6$ cells/mouse). On third and forth days, BSA was dissolved in PBS at a concentration of 10 mg/ml, and the solution was orally administered (1 mg (100 μl)/mouse) to (2) to (5). On 33rd and 34th days, in a manner similar to that on the third and forth days, BSA was orally administered (1 mg/mouse). Five days after the administration, BSA was dissolved in PBS, and the solution was intradermally administered to the earlobe, followed by measuring the thickness of the mouse earlobe after 24, 48, and 72 hours. As a result, in (5) BSA+*L. casei* subsp. *casei*+dextran group, the thickness of the earlobe significantly increased. (See FIG. 3)

Example 6

Figure 4:
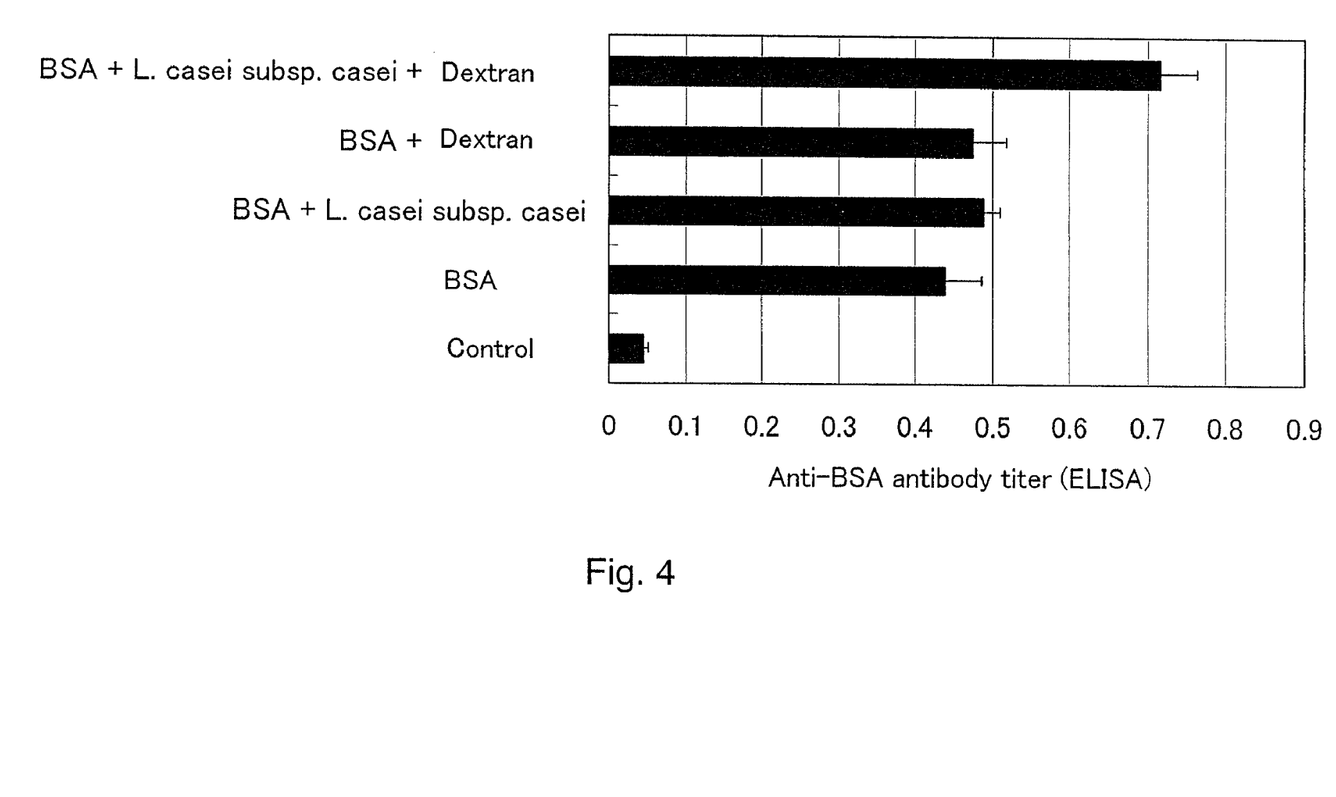
FIG. 4 is a drawing showing the results of enhancing humoral immunity by a dextran in the case of subcutaneously administering the antigen.

Enhancement of Humoral Immunity by Dextran in Subcutaneous Administration of Antigen 30 eight-week-old BALB/c male mice were divided into five groups of six each. Those groups were referred to as (1) control group, (2) BSA group, (3) BSA+*L. casei* subsp. *casei* group, (4) BSA+dextran group, and (5) BSA+*L. casei* subsp. *casei*+dextran group. Over the test period from the beginning of the test, a conventional feed was given to each of (1), (2), and (3), while a dextran-added conventional feed (75 mg dextran/kg conventional feed) and the resultant feed was given to each of (4) and (5). Over the period of three days from the beginning of the test, *L. casei* subsp. *casei* bacteria cells were orally inoculated to (3) and (5) ($10^6$ cells/mouse). On a third day, using FIA (Freund's incomplete adjuvant), PBS (phosphate buffered saline) (PBS+FIA) or BSA (5 mg/ml) (BSA+FIA) was emulsified at a ratio of 1:1, and the emulsion of PBS+FIA was subcutaneously administered to the footpads of the (1) and the emulsion of BSA+FIA was subcutaneously administered to those of the (2) to (5), respectively (200 μl/mouse). On a 35th day, booster was performed in a manner similar to that on the third day. Five days after the booster, the blood was drawn from the suborbital vein, and the anti-BSA antibody titer was determined by ELISA. As a result, in (5) BSA+*L. casei* subsp. *casei*+dextran group, the specific antibody titer was significantly high. (See FIG. 4)

Example 7

Figure 5:
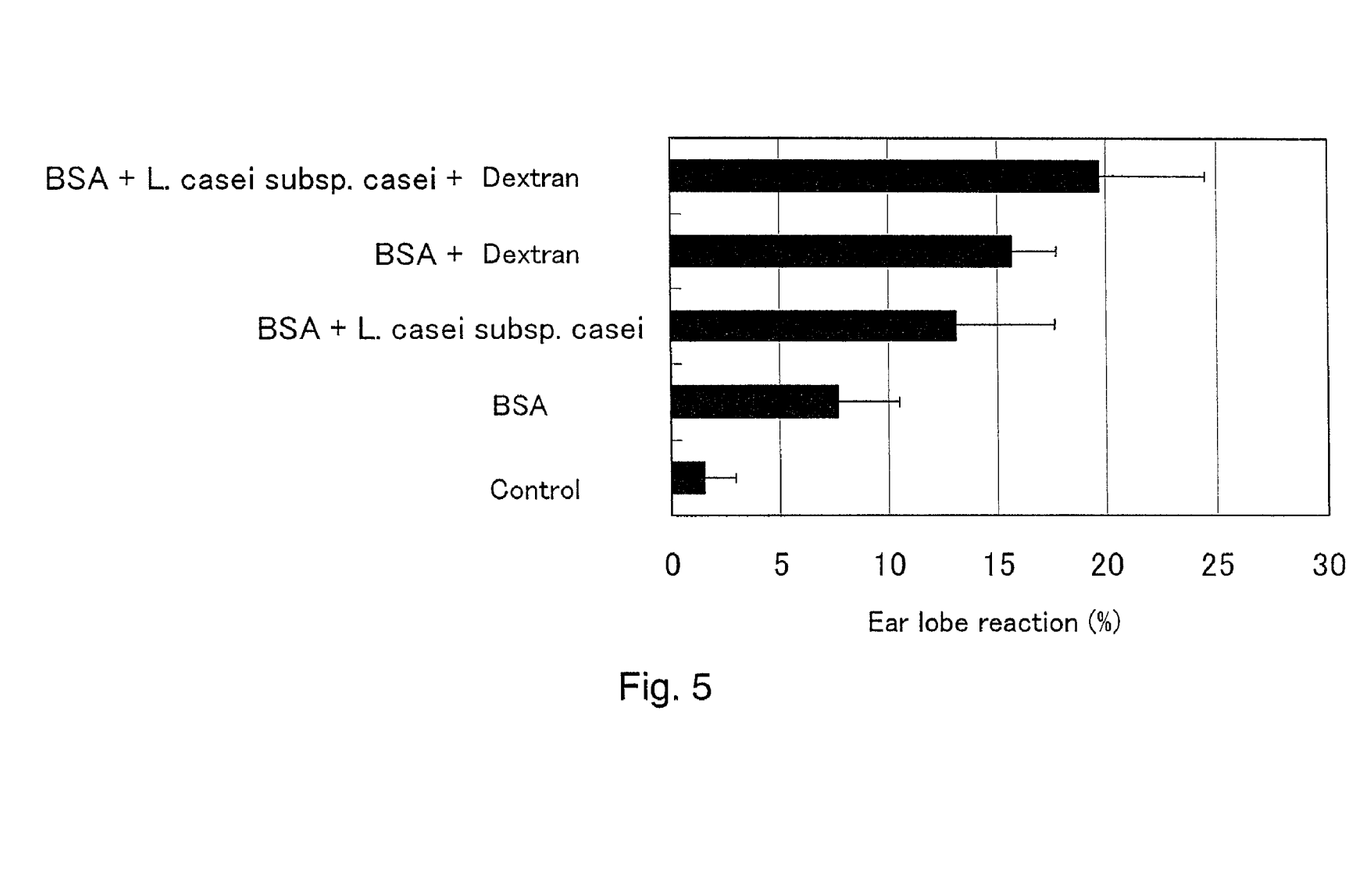
FIG. 5 is a drawing showing the results of enhancing cellular immunity by a dextran in the case of subcutaneously administering the antigen.

Enhancement of Cellular Immunity by Dextran in Subcutaneous Administration of Antigen 30 eight-week-old BALB/c male mice were divided into five groups of six each. Those groups were referred to as (1) control group, (2) BSA group, (3) BSA+*L. casei* subsp. *casei* group, (4) BSA+dextran group, and (5) BSA+*L. casei* subsp. *casei*+dextran group. Over the test period from the beginning of the test, a conventional feed was given to each of (1), (2), and (3), while a dextran-added conventional feed (75 mg dextran/kg conventional feed) was given to each of (4) and (5). Over the period of three days from the beginning of the test, *L. casei* subsp. *casei* bacteria cells were orally inoculated to (3) and (5) ($10^6$ cells/mouse). On a third day, using FIA, PBS (PBS+FIA) or BSA (5 mg/ml) (BSA+FIA) was emulsified at a ratio of 1:1, and the emulsion of PBS+FIA was subcutaneously administered to the footpads of the (1) and the emulsion of BSA+FIA was subcutaneously administered to those of the (2) to (5), respectively (200 μl/mouse). On a 35th day, booster was performed in a manner similar to that on the third day. Five days after the booster, BSA was dissolved in PBS, and the solution was intradermally administered to the mouse earlobe, followed by measuring the thickness of the earlobe after 24, 48, and 72 hours. As a result, in (5) BSA+*L. casei* subsp. *casei*+dextran group, the thickness of the earlobe significantly increased. (See FIG. 5)

INDUSTRIAL APPLICABILITY

According to the present invention, a variety of biological activities originated from *L. casei* subsp. *casei* can be sustained in a living body by selectively growing-proliferating and colonizing *L. casei* subsp. *casei* in the intestine of a human being, animal, or the like or by selectively growing-proliferating *L. casei* subsp. casei in the intestine, without supplying *L. casei* subsp. *casei* at all times.

What is claimed is:

1. A method for selectively proliferating *Lactobacillus casei* subsp. *casei* in the intestine of a subject, comprising:
    orally administering a composition consisting essentially of a dextran and *Lactobacillus casei* subsp. *casei* to the subject, whereby *Lactobacillus casei* subsp. *casei* is proliferated in the intestine of the subject.

2. The method according to claim 1, wherein the dextran has a molecular weight of 2,000 to 40,000,000.

3. A method for enhancing humoral and cellular immunity in a subject in need thereof, comprising:
    selectively proliferating *Lactobacillus casei* subsp. *casei* in the intestine of the subject by orally administering a pharmaceutical composition consisting essentially of a dextran and *Lactobacillus casei* subsp. *casei* to the subject, whereby humoral and cellular immunity are enhanced.

4. The method according to claim 3, wherein the dextran has a molecular weight of 2,000 to 40,000,000.

* * * * *